(12) United States Patent
Hornung et al.

(10) Patent No.: US 7,918,959 B2
(45) Date of Patent: Apr. 5, 2011

(54) METHOD FOR THE PRODUCTION OF A DIAPER

(75) Inventors: Fridmann Hornung, Santiago (CL); Ruediger Kesselmeier, Herbrechtingen (DE); Wolfgang Ostertag, Gerstetten (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 12/624,116

(22) Filed: Nov. 23, 2009

(65) Prior Publication Data

US 2010/0065199 A1     Mar. 18, 2010

Related U.S. Application Data

(63) Continuation of application No. PCT/EP2008/004131, filed on May 23, 2008.

(30) Foreign Application Priority Data

May 24, 2007   (DE) .................... 10 2007 024 180

(51) Int. Cl.
  *B29C 65/00*   (2006.01)
  *B32B 37/00*   (2006.01)
  *B32B 38/04*   (2006.01)
  *B32B 38/10*   (2006.01)

(52) U.S. Cl. ........ 156/252; 156/259; 156/265; 156/270; 156/271; 156/302; 156/201; 156/204; 156/227

(58) Field of Classification Search .................. 156/252, 156/259, 265, 270, 271, 302, 201, 204, 227; 2/402
See application file for complete search history.

(56) References Cited

U.S. PATENT DOCUMENTS

| | | | |
|---|---|---|---|
| 3,599,640 A * | 8/1971 | Larson | 604/394 |
| 5,622,581 A | 4/1997 | Ducker et al. | |
| 5,725,714 A * | 3/1998 | Fujioka et al. | 156/259 |
| 7,160,408 B2 | 1/2007 | Otsubo | |
| 7,214,287 B2 | 5/2007 | Shlomi et al. | |
| 7,314,465 B2 * | 1/2008 | Van Gompel et al. | 604/395 |
| 2002/0138056 A1 | 9/2002 | Kuen | |
| 2006/0108054 A1 | 5/2006 | Ukegawa | |

FOREIGN PATENT DOCUMENTS

| | | |
|---|---|---|
| DE | 10 2005 048 868 | 10/2005 |
| DE | 10 2005 032 221 | 1/2007 |
| EP | 1269949 | 1/2003 |
| EP | 1428487 | 6/2004 |
| EP | 1574191 | 9/2005 |
| WO | 03/082168 | 10/2003 |
| WO | 03/094815 | 11/2003 |
| WO | 2005/094746 | 3/2005 |
| WO | 2005/102241 | 11/2005 |

* cited by examiner

*Primary Examiner* — Linda L Gray
(74) *Attorney, Agent, or Firm* — Brinks Hofer Gilson & Lione

(57) ABSTRACT

The disclosure relates to a method for the production of a diaper having a main part comprising a front region, a back region, and a crotch region located there between that comes to rest between the user's legs in the longitudinal direction, and side sections attached on both sides. The method is characterized in that a material web forming the side sections is supplied in the longitudinal direction; the material recesses for attaining an oblique course or contouring of the side sections are formed by placing an opening with a continuous circumferential edge in the material web; the material web is then divided in the longitudinal direction and said separation runs through the opening; sections are removed from the two partial webs transversely to the longitudinal direction in order to form the side sections to be applied on both sides; and the sections are attached to the respective back region and/or to the front region.

17 Claims, 4 Drawing Sheets

Figure 1:
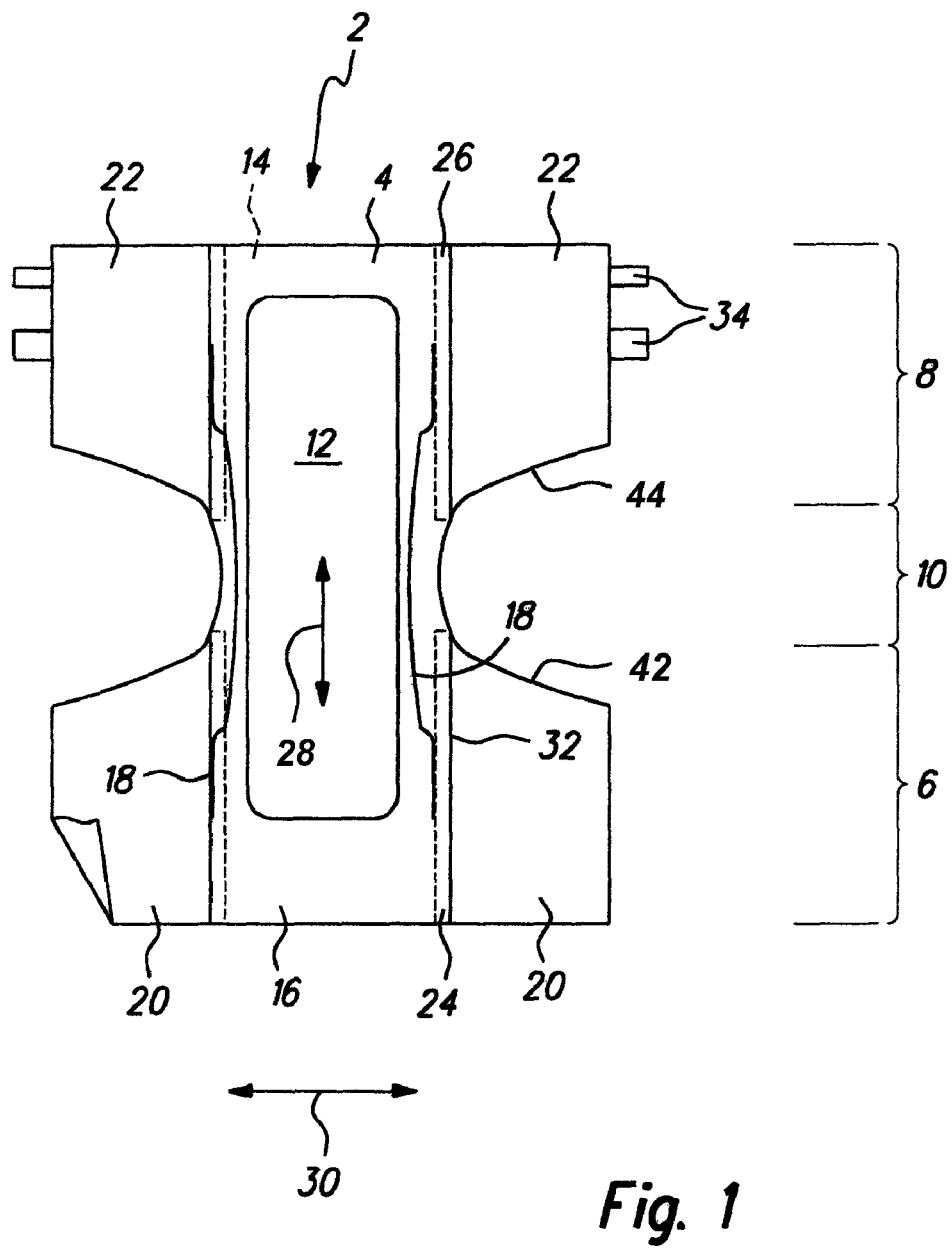

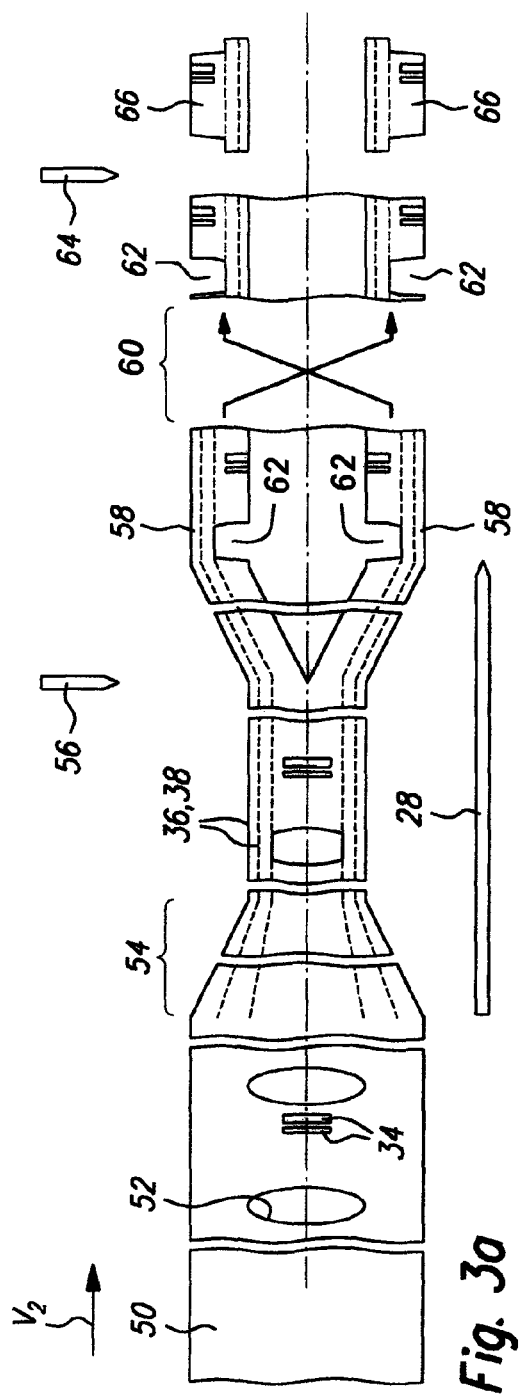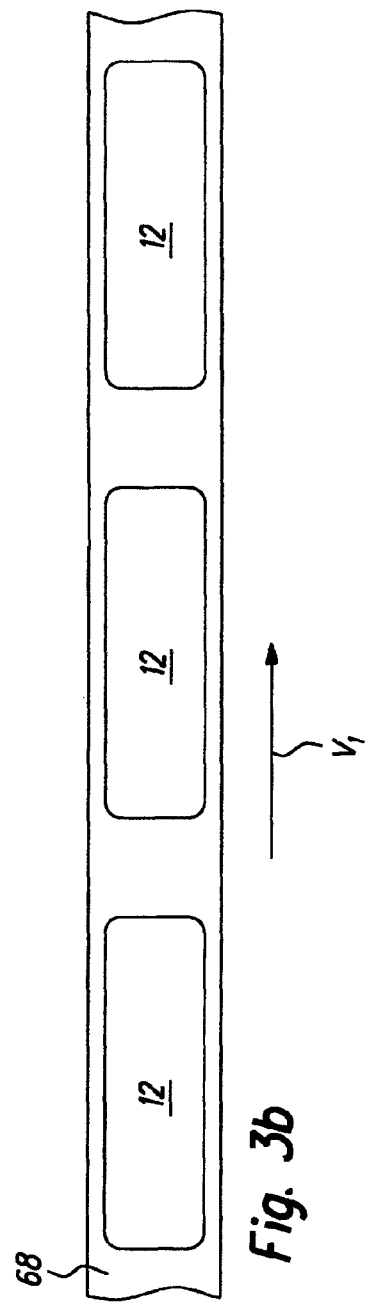
Fig. 3a
Fig. 3b

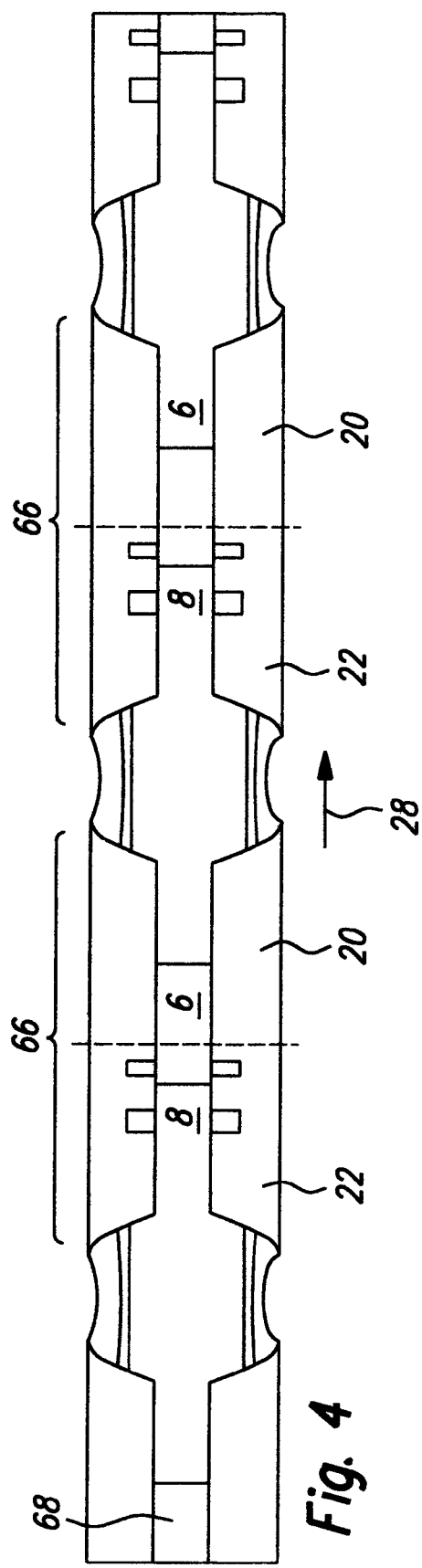
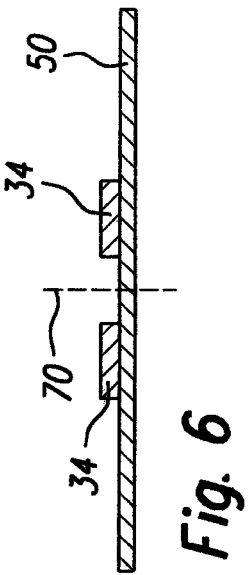

METHOD FOR THE PRODUCTION OF A DIAPER

CROSS-REFERENCE TO RELATED APPLICATIONS

This application is a continuation of International Application No. PCT/EP2008/004131 filed on May 23, 2008, which claims the benefit of DE 10 2007 024 180.3, filed May 24, 2007. The disclosures of the above applications are incorporated herein by reference.

FIELD

The disclosure relates to a method for the production of a diaper or incontinence article.

BACKGROUND

The statements in this section merely provide background information related to the present disclosure and may not constitute prior art.

Diapers are known and described, for example, in WO 2005/102241 A1. Diapers may have a main body comprising a front portion, a back portion, and a crotch portion, said crotch portion being located between said front and back portions and coming to rest between the wearer's legs in the longitudinal direction, wherein the main body includes an absorbent body, the main body having lateral portions attached on both sides to the back portion and/or to the front portion, said lateral portions extending in the transverse direction beyond the lateral longitudinal edges of the main body and connecting the front portion and the back portion to one another in the applied state of the diaper, wherein the lateral portions, at least on the side facing the crotch portion, are configured to run obliquely to the longitudinal direction or contoured, said diaper being produced in its longitudinal direction and, in order to achieve the oblique course or contouring of the lateral portions, material recesses are formed at the lateral portions. They are often used as relatively voluminous incontinence articles for adults. The lateral portions cited above, which are extended in the transverse direction and/or in the circumferential direction of the hip, may be attached to both the front portion and to the back portion of the main body of the diaper, which comprises the absorbent body. It is just as conceivable that the lateral portions are only attached to the front portion or only to the back portion of the main body, that is, for example when the lateral portions in question are applied to the wearer in the circumferential direction of the hip and then attached to one another, thereby forming a kind of belt for the diaper.

Because diapers, or in particular incontinence articles of the type cited above, can have very voluminous lateral portions in the circumferential direction of the hip, the production of these products, in particular transversely to this circumferential direction of the hip, that is in the longitudinal direction of the product, proves very difficult in high-speed production machines, because the materials that form the lateral portions cannot be correctly guided, or only guided with great difficulty in the production machines. "Fluttering," especially of individual sections, or of sections undercut in the direction of the machine, is a problem in production machines.

SUMMARY

We disclose a method for the production of a diaper with a main body comprising a front portion, a back portion, and a crotch portion, said crotch portion being located between said front and back portions and coming to rest between the wearer's legs in the longitudinal direction, wherein the main body includes an absorbent body, the main body having lateral portions attached on both sides to the back portion and/or to the front portion, said lateral portions extending in the transverse direction beyond the lateral longitudinal edges of the main body and connecting the front portion and the back portion to one another in the applied state of the diaper, wherein the lateral portions, at least on the side facing the crotch portion, are configured to run obliquely to the longitudinal direction or contoured, said diaper being produced in its longitudinal direction and, in order to achieve the oblique course or contouring of the lateral portions, material recesses are formed at the lateral portions, by means of which the problems described above in connection with the configuration and attachment of lateral portions may be better controlled.

According to the present disclosure, this is attained with a method, in which the material web forming the bilateral lateral portions is conveyed in the longitudinal direction; in which the material recesses for achieving the oblique course or the contouring of the lateral portions are formed by making an opening with a continuous circumferential edge in the material web; and in which the material web is subsequently divided in partial webs in the longitudinal direction, said separation running through the opening; in which sections are removed from each of the two partial webs transversely to the longitudinal direction in order to form the lateral portions to be applied to both sides; and in which the sections are attached to the respective back portion and/or to the front portion.

Therefore, an opening with a continuous circumferential edge is made in the longitudinal direction of the continuously conveyed material web that forms the lateral portions of the diaper, said opening being, in particular, cut or punched out. After the separation, this opening then forms the oblique course or the contouring of the lateral portions on their side facing the crotch portion of the diaper. The lateral portions, together with the crotch portion of the main body of the diaper then delimit the leg openings of the diaper. The disclosed method is advantageous in that, through the insertion of the above mentioned opening, the material web remains continuously uninterrupted and free from undercutting on the outer edges. In this respect, the material web may be guided without problems. Even if the material web is divided in the longitudinal direction, with a separation or dividing cut running symmetrically through the opening and/or dividing the opening into halves, the material web and/or the partial webs resulting from the longitudinal division remain continuous in the longitudinal direction and/or in the direction of the machine, until it is subsequently separated transversely to the longitudinal direction as lateral portions to be applied.

It should be pointed out at this juncture that after the longitudinal separation of the material web, the two partial webs that result from this operation could then be wound continuously onto a spool and temporarily stored for later use. For further use and application, the continuously wound partial webs are unwound and attached to the front portion and/or the back portion of the main body of the diaper conveyed in the longitudinal direction. This should also be considered to be included in the novelty of the disclosure.

According to an additional novelty of the disclosure, the partial webs resulting from the division of the material web in the longitudinal direction are conveyed in an intersecting manner, resulting in a change of sides in relation to the main body, the separated openings in the two partial webs then both pointing outward. It should, however, be expressly pointed out that the disclosed method may also be implemented without this variation in the method.

Particularly in the case of diapers with very voluminous lateral portions in the circumferential direction of the hip, it is advantageous if the material web is folded onto itself on both sides along at least one folding line that runs in the longitudinal direction. Advantageously, the material web is folded onto itself on both sides along at least two folding lines, in particular along three or four folding lines.

This folding of the material web along a folding line running in the longitudinal direction may be particularly advantageous when the length of the respective lateral portions in a folded state in the transverse direction, that is vertically to the longitudinal direction, extends beyond the longitudinal edge of the main body by at least about 10 cm, in particular by at least about 15 cm, in particular by at least about 18 cm, and additionally in particular by at least about 20 cm.

Partial areas of the lateral portions that are folded about themselves and have surfaces that are in contact with one another may be detachably fixed to one another in this folded configuration, so that there is additional protection against them fluttering apart in the production machine. However, the material sections whose partial sections are folded onto one another may be detachably fixed such that when unfolded, the detachable means of fixation may be undone by means of a single pull from the lateral portions. For this purpose, the detachable means of fixation of the partial sections of the lateral portions that are folded onto one another may consist of thermally and/or ultrasonically produced joints. However, deviating from this or in addition to it, bonding by means of an adhesive is also conceivable and advantageous.

The partial regions or the lateral portions that are folded onto one another may be detachably fixed to one another such that a handling region of the lateral portions remains unfixed and may be easily gripped with the fingers of a wearer or a caregiver. The lateral portions are in particular folded such that this handling region protrudes in a transverse direction beyond the folded configuration.

Particularly in the case of lateral portions with a relatively long extension in the circumferential direction, it is advantageous if the material web is separated transversely to the longitudinal direction in such a manner that the lateral portions in the longitudinal direction in the region of attachment to the main body, have a longitudinal extension of at least about 10 cm, in particular of at least about 14 cm, in particular of at least about 18 cm, and additionally in particular of at least about 22 cm.

In a further development of the disclosure, it is proposed that before the separation of the material web in the longitudinal direction, closing means are applied to the material web and fixed in place. These closing means serve the purpose of closing the diaper in the circumferential direction of the hip when the diaper is applied by the wearer or by caregivers. This may nearly be any kind of adhesively or mechanically functioning closing means (for example hook/loop materials), which may also be conveyed from continuous web materials during the production of the diaper, separated transversely to the conveying direction, and then applied to the diaper to be manufactured and fixed in place (cut and place method).

In this case, it is advantageous if the closing means are applied near or in the region of the division in the longitudinal direction. This is advantageous in terms of production technology because with the disclosed method, the closing means that are assigned to the two respective lateral portions (left/right) are not, as in the state of the art, applied to the outer left and right sides, but rather in proximity to one another, which further reduces costs when the disclosed method is used. In a further development of this novelty of the disclosure, the closing means are applied such that they bridge the subsequent separation process, and are likewise divided in the course of this separation. According to this variation, a section of the corresponding substrate of the closing means forms the closing means on both sides. This is an additional simplification of the method and the device for implementing it.

Although the opening to be made in the material web may have an arbitrary configuration, i.e. be configured round, oval, or rectangular, it has proven advantageous if the opening is formed by a rounded, for example approximately oval contour that is then reproduced in a rounded course of the subsequent lateral portions.

According to a variation of the method, it is conceivable and advantageous for the diapers to be produced such that by consecutively conveying the diapers in the longitudinal direction, the back portion of one diaper follows the back portion of the other diaper, and the front portion of one diaper follows the front portion of the other diaper. Alternatively, it would be conceivable that the back portion of one diaper follows the front area of the other diaper.

Nevertheless, it is advantageous if the separation of the sections from the material web and/or from the partial webs is carried out transversely to the longitudinal direction such that in each case, a section separated transversely to the longitudinal direction forms lateral portions of two diapers that are consecutively conveyed. This would then be one back portion and one back portion, or one front portion and one front portion, or respectively a back portion adjoining a front portion of the consecutively conveyed diapers. In such cases, the separation of the lateral portions of diapers that are consecutively conveyed takes place at the same time as the separation of the diapers from a continuous web in the longitudinal direction.

The material web, and thus the lateral portions that are attached to the main body of the diaper, are made of a nonwoven fabric, in particular, for example, spunbond materials (S) or spunbond meltblown materials (SM), or meltblown layers provided on both sides with spunbond materials (SMS), or carded nonwoven materials may be used. Nonwoven laminates, that is in particular, two-layer, three-layer, or multiple-layer combinations of the above mentioned nonwoven materials may be used. Bonding of the individual layers may be accomplished, for example by means of thermal joining methods (welding, in particular laser welding) or by means of ultrasonic welding; cold pressing, needling, sewing, or gluing of nonwoven materials are also conceivable). The lateral portions joined laterally to the main body of the diaper are configured at least partially as breathable, in which case microporosity is seen as an advantage that allows both air exchange and the outward passage of moisture in the form of water vapor. The lateral portions advantageously have a grammage of about 10 to about 150 $g/m^2$, in particular of about 10 to about 100 $g/m^2$, and additionally in particular of about 20-50 $g/m^2$.

It may also be advantageous, if the lateral portions of the front portion and the back portion are configured differently. They may, for example, differ with regard to the type, composition or arrangement of the closing means, or they may differ with regard to the material and/or the grammage, and/or the breathability of the material web used. In the latter case, a continuous material web is conveyed and processed in each case in order to produce the lateral portions in the front portion and in the back portion.

It has proven advantageous, if the main body web forming the main body is conveyed at a speed v1 of about 100-600 m/min., in particular of about 110-500 m/min., and further in particular of about 120-400 m/min.

Furthermore, it has proven advantageous, if the material web forming the lateral portions is supplied at a speed v2 of about 50-300 m/min., in particular of about 55-250 m/min., and further in particular of about 60-200 m/min.

It is particularly advantageous, if the ratio of v2 to v1 amounts to about 0.25-0.75, in particular about 0.30-0.65, in particular about 0.35-0.65, in particular about 0.40-0.60, and further in particular about 0.45-0.55.

Further areas of applicability will become apparent from the description provided herein. It should be understood that the description and specific examples are intended for purposes of illustration only and are not intended to limit the scope of the present disclosure.

DRAWINGS

Figure 2C:
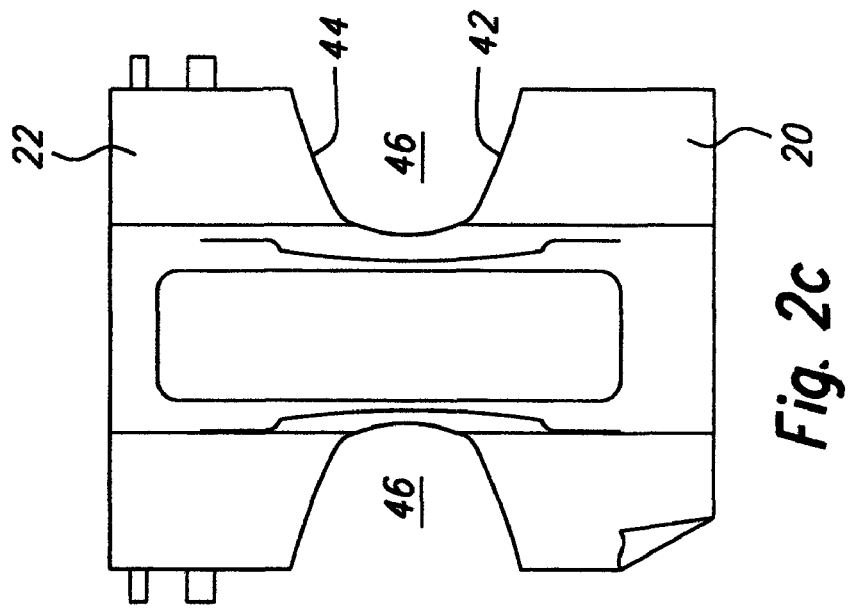
Figure 2B:
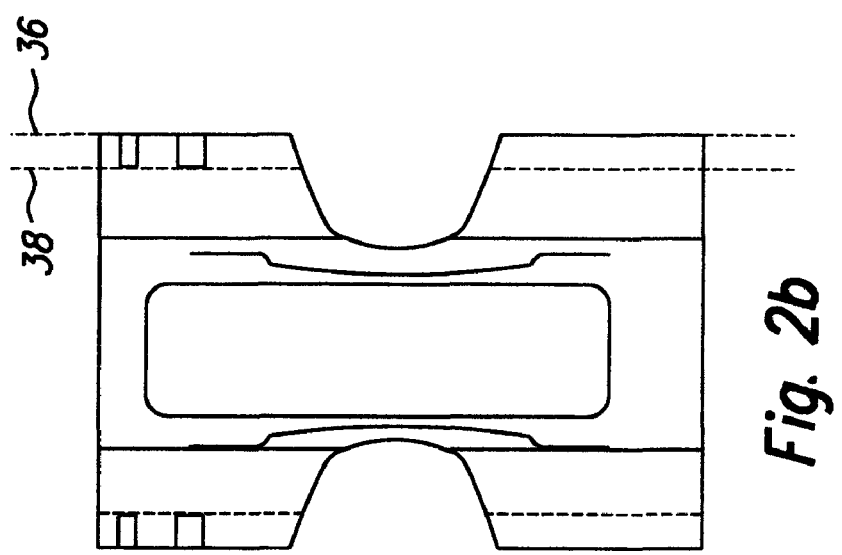
Figure 2A:
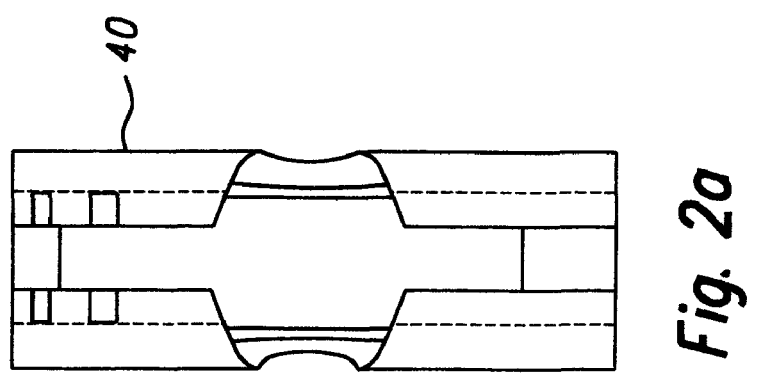

In order that the disclosure may be well understood, there will now be described various forms thereof, given by way of example, reference being made to the accompanying drawings, in which:

FIG. 1: a schematic representation of a diaper to be produced using the principles of the disclosure, as a top view;

FIGS. 2a to c: different folded states of the diaper according to FIG. 1;

FIG. 3a: a schematic representation of the production method according to the principles of the disclosure, showing the conveyance of the material web forming the lateral portions;

FIG. 3b: a schematic representation of the production method according to the principles of the disclosure, showing the conveyance of a main web that forms the main body;

FIG. 4: a schematic representation of the application of the lateral portions to the diaper;

FIG. 5: a schematic sectional view through a material web with applied closing means according to a variation; and FIG. 6: a schematic sectional view through a material web with applied closing means according to another variation.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

FIGS. 1 and 2 show diaper 2 produced in the disclosed manner in different folded states. The diaper 2 comprises a main body designated with the reference numeral 4, which is often also referred to as a chassis. The main body is comprised of a front portion 6, a back portion 8, and a crotch portion 10 placed between them, and which is located between the legs of the wearer when the diaper 2 is applied to the wearer. The main body 4 also comprises an absorbent body 12, which is dimensioned for the absorption and permanent storage of body fluids in a suitable manner. The absorbent body 12 is normally underlaid by a liquid-impervious layer 14, which may also form the external visible face of the incontinence article. In addition, the absorbent body 12 is usually overlaid with a liquid-pervious layer 16 (topsheet). Also shown are elastifying elements 18 running on both sides of the absorbent body 12, which may include tensioned elastically extensible materials. In particular, the main body 4 may include laterally projecting barrier means, which form a means of protection against lateral leaking and which flank the absorbent body. These projecting barrier means also include elastically pretensioned elastifying means. The components of the diaper 2 described above form the main body 4, or are to be assigned to the main body 4.

In addition, the diaper 2 comprises the lateral portions 20 and 22 that are inseparably attached to the front portion 6 and the back portion 8. The lateral portions 20, 22 are inseparably attached to longitudinal edge sections 24 and 26 of the main body 4. The lateral portions 20, 22 extend in the circumferential direction of the hip beyond a longitudinal lateral edge 32 of the main body 2 in a vertical transverse direction 30 to the longitudinal direction 28 of the diaper 2. The lateral portions 20, 22 are placed around the user when applying the diaper 2 in the circumferential direction of the hip and are normally closed on top of one another. In order to fix the lateral front and back portions 20, 22 to one another, closing means 34 of a known type are provided, which are therefore not described in detail, said closing means being indicated on the lateral portions 22 of the back portion 8 by way of example in the represented case.

It would also be conceivable for the diaper 2 to have lateral portions only in the front portion 6 or only in the back portion 8, said lateral portions, however, then being more voluminous in the transverse direction 30 than outlined above, so that they could be closed on themselves in the circumferential direction of the hip, or on the main body 4 of the diaper 2.

As can be seen in FIGS. 2a to 2c, the respective lateral portions 20, 22 are folded onto themselves in the longitudinal direction 28, creating Z-shaped or accordion-shaped folds. This folded configuration, as shown in FIG. 2a, is then folded onto the main body 4 around an additional fold line 40 that runs approximately along the longitudinal lateral edge 32 of the main body 4.

It can be seen in FIGS. 1 and 2a-2c that the lateral portions 20, 22 run obliquely to the longitudinal direction 28 on their side facing the crotch portion 10, and/or the side that partially borders the crotch region 10. One edge 42, and/or 44, of the lateral portions 20, 22 therefore does not run precisely in the transverse direction 30, but at an angle to it and/or at an angle to the longitudinal direction 28, forming a arched contour. The edge 42 or 44 could, however, also be straight, but still run obliquely to the longitudinal direction 28 and/or in the transverse direction 30, forming wedge-shaped lateral portions and leg openings 46.

A material web forming the lateral portions 20, 22 may be continuously conveyed in the longitudinal direction.

In such case, the edges 42, 44 are formed by cutting operations, i.e. material recesses are provided in the material web, said recesses becoming the crotch portion 10 and/or the leg openings 46 of the diaper 2 to be produced. The disclosed method applied for this purpose will now be described on the basis of FIG. 3:

FIG. 3a schematically shows the feeding and configuration of a material web 50, from which the front and/or the back side-sections 20, 22 of the diaper 2 are made. FIG. 3b is a schematic depiction of the feeding of the main body web 68 that forms the main body 4 of the diaper at a speed v1. The material web 50 is conveyed in the longitudinal direction 28 (longitudinal production) at a speed v2. In order to produce the later contouring of the lateral portions 20, 22 on their sides facing the crotch portion 10, an opening 52 is cut in the material web 50 in such a way that this opening 52 in the plane of the material web 50 is completely circumferentially surrounded. Before or after the opening 52 is made, closing means 34 are applied in the direction of production between two consecutive openings 52 in the represented exemplary case shown. In this case, known adhesive and/or mechanically adhering closing means 34, for example in the form of strip-shaped closing tapes are used.

In a folding station 54, the material web 50 is folded inward on both sides onto itself around a plurality of fold lines 36, 38 running in the longitudinal direction 28 from the outside, so that a Z or leporello-shaped folding results. In a cutting station 56, the material web 50 is cut in the longitudinal direction 28, so that two partial webs 58 are conveyed onward in the longitudinal direction.

In a crossing station 60, the partial webs 58 are intersecting one another, resulting in a change of sides relative to the direction of production and/or relative to a main body web that is not shown in FIG. 3. Separation in the longitudinal direction takes place in such a way that the separation process may take place through the center or symmetrically through the openings 52, so that open-edged material recesses 62 are formed.

It may be seen that the open-edged material recesses 62 now point outward, away from one another.

In a separating station 64, the partial webs 58, which are still continuous in the longitudinal direction are cut transversely to the longitudinal direction 28 into sections 66. These sections 66 may then be applied to the main body web 68 that is shown in FIG. 3b and inseparably fixed there to the longitudinal edge sections 24, 26 of the later main body 4 of the diaper.

Regarding the schematically represented sections 66 shown in FIG. 3a, after separation from the continuous partial web 58, they may be a lateral portion to be assigned to a single diaper, or it would be conceivable that these sections could form lateral portions of two diapers that are consecutively conveyed in the longitudinal direction and/or in the production direction. In the latter case, during final separation of the diapers, the lateral portions would then be advantageously cut off a continuous web, in this case likewise transversely to the longitudinal direction. A process of this kind is schematically represented in FIG. 4. It may be seen that the sections 66, which are used to form the lateral portions 20, 22 are applied to a continuous main body web 68, which forms the main body of the diaper, and then folded inward. Each section 66 comprises the lateral portions 20, 22 of two diapers that are consecutively conveyed in the longitudinal direction 28 and/or in the production direction. In the process according to FIG. 4, the diapers are produced in such a way that in the case of diapers that are consecutively conveyed in the longitudinal direction 28, the back portion 8 of one diaper follows the front portion 6 of the other diaper.

Web speeds v1 of the main body web 68 forming the lateral portions 20, 22, may be about 100-600 m/min., in particular of about 110-500 m/min., and further in particular of about 120-400 m/min. Web speeds v2 of the material web 50 forming the lateral portions 20, 22 may be about 50-300 m/min., in particular about 55-250 m/min., and further in particular of about 60-200 m/min. The ratio of v2 to v1 may be about 0.25-0.75, in particular about 0.30-0.65, in particular about 0.35-0.65, in particular about 0.40-0.60, and further in particular about 0.45-0.55.

It would also be conceivable that two of the configuration lines shown in FIG. 3a could be implemented in one production process of a diaper, wherein one line produces the lateral portions of the front portion, and the other line produces the lateral portions of the back portion of the diaper. In this way, different web materials may be used to form the lateral portions in the front portion and in the back portion. It was pointed out above that the step of intersecting the partial webs 58 is not absolutely necessary. The lateral portions could also be applied and fixed to a web conveying the main bodies in the assembly upstream of the crossing station 62 and then—if required—turned over toward the outside.

The disclosed method achieves that the material web 50 and/or the partial webs 58 are continuously conveyed in the production direction after the longitudinal separation, and that the open-edged material recesses 62 only appear after the longitudinal separation of the material web 50. Until then, the openings 52 are completely surrounded and may therefore be transported in a positionally stable manner without the occurrence of disruptive fluttering of the materials. With the disclosed process, the production step with open-edge material recesses 62 is minimized compared to the state of the art. This results in a considerable improvement of the production method. Moreover, it is also advantageous that closing means 34 for the lateral portions on both sides may be applied in one operation. The longitudinal separation, as described above, then includes these closing means 34 as well. This is represented schematically in FIG. 5, where the drawing plane runs vertical to the production direction, and the broken line in FIG. 5 represents the longitudinal separation plane 70 of the cutting station 56. FIG. 6 schematically shows the positioning of the closing means 34 on the material web 50 in the region of the longitudinal separation plane 70, whereby the closing means 34, in contrast to FIG. 5, do not bridge the longitudinal separation plane 70.

It should be noted that the disclosure is not limited to the variations described and illustrated as examples. A large variety of modifications have been described and more are possible applying the principles of the disclosure. These and further modifications as well as any replacement by technical equivalents may be added to the description and figures, without leaving the scope of the protection of the disclosure and of the present patent.

What is claimed is:

1. A method for the production of a diaper with a main body, consisting of a front portion, a back portion and a crotch portion that lies between them, and placed in a longitudinal direction between legs of a wearer, wherein the main body comprises an absorbent body and lateral portions that are attached on both sides to the back portion and/or to the front portion, said lateral portions extending in a transverse direction beyond lateral longitudinal edges of the main body and connecting the front portion and the back portion to one another in an applied state of the diaper, wherein the lateral portions, at least on the side facing the crotch portion, are configured in such a way that they run obliquely to the longitudinal direction or are contoured to form a leg opening portion, said diaper being produced in its longitudinal direction, and in order to achieve the oblique course or contouring of the lateral portions, material recesses are formed at the lateral portions, characterized in that a material web that forms one of the lateral portions on both sides is conveyed in the longitudinal direction; that the material recesses for achieving the oblique course or the contouring of the lateral portions are formed by making an opening with a continuous circumferential edge in the material web; that subsequently, the material web is divided in the longitudinal direction into partial webs, the separation running through the opening; that sections are cut from the two partial webs, in each case transversely to the longitudinal direction in order to form the lateral portions that are to be applied to both sides, and that the sections are attached to the respective back portion and/or front portion, wherein the partial webs that are formed by the division in the longitudinal direction are supplied such that they intersect one another, so that there is a change of side in relation to the main body, and divided openings then face in each case outward as material recesses in the two partial webs.

2. The method according to claim 1, characterized in that the material web is folded on both sides onto itself around at least one folding line that runs in a longitudinal direction.

3. The method according to claim 1, characterized in that the opening is approximately oval in shape.

4. The method according to claim 1, characterized in that the diapers are produced in such a way that when the diapers are consecutively conveyed in the longitudinal direction, the back portion of one diaper follows the back portion of the other diaper, and the front portion of one diaper follows the front portion of the other diaper.

5. The method according to claim 1, characterized in that the diapers are produced in such a way that when the diapers are consecutively conveyed in the longitudinal direction, the back portion of one diaper follows the front portion of the other diaper.

6. The method according to claim 1, characterized in that each section that was cut off transversely to the longitudinal direction forms lateral portions of two consecutively conveyed diapers.

7. The method according to claim 1, characterized in that the lateral portions of the front portion and the back portion are differently configured.

8. The method according to claim 1, characterized in that the lateral portions are different from the front portion and the back portion with regard to at least one of the material, the grammage, and the breathability of the material web used.

9. The method according to claim 1, characterized in that a material web forming the main bodies is conveyed at a speed v1 of about 100-600 m/min.

10. The method according to claim 1, characterized in that a material web forming the main bodies is conveyed at a speed v1 of about 110-500 m/min.

11. The method according to claim 1, characterized in that a material web forming the main bodies is conveyed at a speed v1 of about 120-400 m/min.

12. The method according to claim 1, characterized in that the material web forming the lateral portions is supplied at a speed v2 of about 50-300 m/min.

13. The method according to claim 1, characterized in that the material web forming the lateral portions is supplied at a speed v2 of 55-250 m/min.

14. The method according to claim 1, characterized in that the material web forming the lateral portions is supplied at a speed v2 of about 60-200 m/min.

15. The method according to claim 1, characterized in that a material web forming the main bodies is conveyed at a speed v1 and the material web forming the lateral portions is supplied at a speed v2, and further wherein the ratio of v2 to v1 is at least one of about 0.25-0.75, about 0.30-0.65, about 0.35-0.65, about 0.40-0.60, and about 0.45-0.55.

16. A method for the production of a diaper with a main body, consisting of a front portion, a back portion and a crotch portion that lies between them, and placed in a longitudinal direction between legs of a wearer, wherein the main body comprises an absorbent body and lateral portions that are attached on both sides to the back portion and/or to the front portion, said lateral portions extending in a transverse direction beyond lateral longitudinal edges of the main body and connecting the front portion and the back portion to one another in an applied state of the diaper, wherein the lateral portions, at least on the side facing the crotch portion, are configured in such a way that they run obliquely to the longitudinal direction or are contoured to form a leg opening portion, said diaper being produced in its longitudinal direction, and in order to achieve the oblique course or contouring of the lateral portions, material recesses are formed at the lateral portions, characterized in that a material web that forms one of the lateral portions on both sides is conveyed in the longitudinal direction; that the material recesses for achieving the oblique course or the contouring of the lateral portions are formed by making an opening with a continuous circumferential edge in the material web; that subsequently, the material web is divided in the longitudinal direction into partial webs, the separation running through the opening; that sections are cut from the two partial webs, in each case transversely to the longitudinal direction in order to form the lateral portions that are to be applied to both sides, and that the sections are attached to the respective back portion and/or front portion, wherein the closing means are applied to the material web and fixed there before dividing the material web in the longitudinal direction and the closing means bridge a course of a subsequent division, and is likewise cut through.

17. The method according to claim 16, characterized in that the closing means are applied near to or in the region of a separation plane that surrounds the longitudinal direction.

* * * * *